(12) United States Patent
Reinherz et al.

(10) Patent No.: US 6,416,971 B1
(45) Date of Patent: Jul. 9, 2002

(54) SOLUBLE SINGLE CHAIN T CELL RECEPTORS

(75) Inventors: Ellis L. Reinherz, Lincoln, MA (US); Jiri Novotny, Princeton, NJ (US); Stephen T. Smiley, Boston, MA (US); Ping Li, Cambridge, MA (US); Ramesh Ganju, Boston, MA (US)

(73) Assignees: E.R. Squibb & Sons, Inc., Princeton, NJ (US); Dana Farber Cancer Institute, Boston, MA (US)

(*) Notice: Subject to any disclaimer, the term of this patent is extended or adjusted under 35 U.S.C. 154(b) by 0 days.

(21) Appl. No.: 07/695,141

(22) Filed: May 8, 1991

Related U.S. Application Data

(63) Continuation-in-part of application No. 07/523,632, filed on May 15, 1990, now abandoned.

(51) Int. Cl.[7] .................................................. C12P 21/03
(52) U.S. Cl. ................................................... 435/69.1
(58) Field of Search ............................ 435/69.7, 252.3, 435/320.1; 530/350; 536/27, 23.4

(56) References Cited

U.S. PATENT DOCUMENTS

| 4,713,332 A | 12/1987 | MAk |
| 4,874,845 A | 10/1989 | Saito et al. |
| 4,923,799 A | 5/1990 | Mak |
| 4,946,778 A | * 8/1990 | Ladner et al. |

FOREIGN PATENT DOCUMENTS

| WO | WO 8801649 | 3/1988 |
| WO | WO 8809344 | 12/1988 |
| WO | WO 8903996 | 5/1989 |

OTHER PUBLICATIONS

Science, 238:1704–1707, Dec. 18, 1987, Smith et al Blocking of HIV–1 Infectivity by a Soluble, Secreted Form of the CD4 Antigen.*
Nature, 339:394–397, Jun. 1, 1989, Chaudhary et al A Recombinant Immunotoxin Consisting of Two Antibody Domains Fused to Pseudomonas Exotoxin.*
Cell, 58:911–921, Sep. 8, 1989, Becker et al Expression of a Hybrid Immunoglobulin–T cell Receptor Protein in Transgenic Mice.*
J. Biol. Chem. 269:7310–7316, May 5, 1989, Mariuzza et al Secretion of a Homodimeric $V_\alpha C_\kappa$ T–cell Receptor–Immunoglobulin Chimeric Protein.*
Nakauchi, H. et al., Proc. Natl. Acad. Sci. USA 84, 4210–4214 (1987). "Molecular cloning of Lyt–3, a membrane glycoprotein marking a subset of mouse T lymphocytes: Molecular homology to immunogobulin and T–cell receptor variable and joining regions".
Bird, Robert E., et al. Science 242, 423–426 (1988) "Single Chain Antigen–Binding Proteins".
Huston, James S., et al., Proc. Natl. Acad. Sci. USA, vol. 85, 5879–5883 (1988), "Protein engineering of antibody binding sites: Recovery of specific activity in an anti–digoxin single–chain Fv analogue produced in *Escherichia coli*".
Skerra, Arne, et al., Science, vol. 240, 1038–1041 (1988), "Assembly of a Functional Immunoglobulin Fv Fragment in *Escherichia coli*".

(List continued on next page.)

Primary Examiner—John Ulm
(74) Attorney, Agent, or Firm—Rosemarie R. Wilk-Oresca; Christopher A. Klein

(57) ABSTRACT

Soluble, single chain T cell receptors, nucleic acid sequences, particularly DNA sequences, encoding the soluble, single chain T cell receptor, expression vectors containing the DNA sequences, and host cells containing the expression vectors.

16 Claims, 7 Drawing Sheets

OTHER PUBLICATIONS

Better, Marc, et al., Science vol. 240, 1041–1043 (1988), "*Escherichia coli*Secretion of an Active Chimeric Antibody Fragment".

Vandenbark, A. A. et al., Nature 341, 544–546 (1989), "Immunization with a synthetic T–cell receptor V–region peptide protects against experimental autoimmune encephalomyelitis".

Janeway, C. A., Nature 341, 482–483 (1989), "Immunotherapy By peptides?".

Orlandi, R. et al., Proc. Natl. Acad. Scie. USA 86, 3833–3837 (1989), "Cloning immunoglobulin variable domains for expression by the polymerase chain reaction".

Urban, J. L. et al., Cell 54, 577–592 (1988), "Restricted Use of T Cell Receptor V Genes in Murine Autoimmune Encephalomyelitis Raises Possibilities for Antibody Therapy".

Duffaud, G. D., Methods in Enzymology 153, 492–507 (1987), "Expression and Secretion of Foreign Proteins in *Escherichia coli*".

Takahara, M. et al., J. Biol. Chem. 260, 2670–2674, (1985) "The ompA Signal Peptide Directed Secretion of Staphylococcal Nuclease A by Escherichia coli".

Li, P. et al., Proc. Natl. Acad. Sci. USA 85, 7685–7689, (1989) "Alteration of the amino terminus of the mature sequence of a periplasmic protein can severely affect protein export in *Escherichia coli*".

Kuwana, Y. et al., Biochem. Biophys. Res. Commun. 149, 960–968 (1987), "Expression of Chimeric Receptor Composed of Immunoglobulin–Derived V Resions and T–Cell Receptor–Derived C Regions".

Mariuzza, R.A. and Winter, G., J. Biol. Chem. 264, 7310–7316 (1989) "Secretion of Homodimeric $V_\alpha C_\kappa$ T–Cell Receptor–Immunoglobulin Chimeric Protein".

Gascoigne, N.R. J. et al., Proc. Natl. Acad. Sic. USA 84, 2936–2940 (1987) "Secretion of a chimeric T–cell receptor–immunoglobulin protein".

Gross, G. et a., Transplantation Proceedings, 21, 127–130 (1989) "Generation of Effector T–Cells Expressing Chimeric T–Cell Receptor with Antibody Type–Specificity".

Davis, M.M. and Bjorkman, P.J., Nature 334, 395–402 (1988) T–Cell antigen receptor genes and T–Cell Recognition.

Traunecker, A. et al., Immunol. Today 10, 29–32 (1989) "Solubilizing the T–Cell Receptor–Problems in Solution".

Ward, E. S. et al., Nature 341, 544–546 (1989) "Binding activities of a repertoire of single immunoglobulin variable domains secreted from *Escherichia coli*".

* cited by examiner

```
        EcoRI
     GAA TTC ATG AAT GCT GGT GTC ACT CAG ACC CCA AAA TTC CGG GTC CTG AAG ACA
-3   (e) (f) (m) Asn Ala Gly Val Thr Gln Thr Pro Lys Phe Arg Val Leu Lys Thr

GGA CAG AGC ATG ACA CTG CTG TGT GCC CAG GAT ATG AAC CAT GAA TAC ATG TAC
+16  Gly Gln Ser Met Thr Leu Leu Cys Ala Gln Asp Met Asn His Glu Tyr Met Tyr

TGG TAT CGA CAA GAC CCA GGC ATG GGG CTG AGG CTG ATT CAT TAC TCA GTT GGT
+34  Trp Tyr Arg Gln Asp Pro Gly Met Gly Leu Arg Leu Ile His Tyr Ser Val Gly

GAG GGT ACA ACT GCC AAA GGA GAG GTC CCT GAT GGC TAC AAT GTC TCC AGA TTA
+52  Glu Gly Thr Thr Ala Lys Gly Glu Val Pro Asp Gly Tyr Asn Val Ser Arg Leu

AAA AAA CAG AAT TTC CTG CTG GGG TTG GAG TCG GCT GCT CCC TCC CAA ACA TCT
+70  Lys Lys Gln Asn Phe Leu Leu Gly Leu Glu Ser Ala Ala Pro Ser Gln Thr Ser

GTG TAC TTC TGT GCC AGC AGG ACG GCC ACG CAG CCC CAG CAT TTT GGT GAT GGG
+88  Val Tyr Phe Cys Ala Ser Arg Thr Ala Thr Gln Pro Gln His Phe Gly Asp Gly

AvaI
     ACT CGA CTC TCC ATC CTA CCC GGG GGC GGT GGT TCT GGT GGT GGT GGT TCT GGT
106  Thr Arg Leu Ser Ile Leu Pro Gly Gly Gly Gly Ser Gly Gly Gly Gly Ser Gly

NarI
     GGT GGT GGT TCT GGT GGT GGT GGT TCT GGC GCC CAG CAG CAG GTG AAA CAA AGT
124  Gly Gly Gly Ser Gly Gly Gly Gly Ser Gly Ala Gln Gln Gln Val Lys Gln Ser

CCT CAA TCT TTG ATA GTC CAG AAA GGA GGG ATT TCA ATT ATA AAC TGT GCT TAT
142  Pro Gln Ser Leu Ile Val Gln Lys Gly Gly Ile Ser Ile Ile Asn Cys Ala Tyr

GAG AAC ACT GCG TTT GAC TAC TTT CCA TGG TAC CAA CAA TTC CCT GGG AAA GGC
160  Glu Asn Thr Ala Phe Asp Tyr Phe Pro Trp Tyr Gln Gln Phe Pro Gly Lys Gly

CCT GCA TTA TTG ATA GCC ATA CGT CCA GAT GTG AGT GAA AAG AAA GAA GGA AGA
178  Pro Ala Leu Leu Ile Ala Ile Arg Pro Asp Val Ser Glu Lys Lys Glu Gly Arg

TTC ACA ATC TCC TTC AAT AAA AGT GCC AAG CAG TTC TCA TTG CAT ATC ATG GAT
196  Phe Thr Ile Ser Phe Asn Lys Ser Ala Lys Gln Phe Ser Leu His Ile Met Asp

TCC CAG CCT GGA GAC TCA GCC ACC TAC TTC TGT GCA GCA AGC TTT TCA GGA AAC
214  Ser Gln Pro Gly Asp Ser Ala Thr Tyr Phe Cys Ala Ala Ser Phe Ser Gly Asn

PvuII
     ACA CCT CTT GTC TTT GGA AAG GGC ACA AGA CTT TCT GTG ATT GCA TAA TGA CAG
232  Thr Pro Leu Val Phe Gly Lys Gly Thr Arg Leu Ser Val Ile Ala --- ---
```

FIG. 2B

T-CELL RECEPTOR CHIMERA

A. ILE$_{182}$

B. MET$_{182}$

SOLUBLE SINGLE CHAIN T CELL RECEPTORS

This application is a continuation-in-part of U.S. Ser. No. 07/523,632 filed May 15, 1990 now abandoned.

BACKGROUND OF THE INVENTION

Antigen binding receptors are of two basic types: immunoglobulin molecules (i.e., antibodies) expressed on the surface of B lymphocytes and secreted by plasma cells and T cell receptors on the surface of T lymphocytes.

The T cell receptor (TCR) is a molecular complex consisting of multiple subunits that mediate the recognition of antigen in the context of a particular major histocompatibility complex (MHC) product. Meuer, S. C., et al., Ann. Rev. Immunol. 2, 23–50 (1984); Clevers, H., et al., Ann. Rev. Immunol. 6, 629–662 (1988); Davis, M. M. and P. J. Bjorkman, Nature 334, 395–402 (1988). The antigen/MHC binding moiety, termed Ti, is a disulfide-linked heterodimer of 90 kD consisting of one and one β subunit on the majority of peripheral T lymphocytes. Both subunits are immunoglobulin-like, being composed of variable and constant domains, the former encoding the unique specificity of a given T cell clone. Ti, in turn, is non-covalently associated with a set of four invariant monomorphic subunits (γ, δ, ε and ζ), collectively termed CD3. All six receptor subunits are trans-membrane proteins and all but the ε and ζ subunits possess N-linked glycan moieties. The Ti and β subunits likely form a binding site for antigen and major histocompatability complex (MHC) through interaction of their variable domains whereas the CD3 subunits are thought to subserve signal transduction functions. In addition, it is known that a subpopulation of T cells ($\leq 5\%$ of peripheral T lymphocytes) exist that contain T cell receptors which contain Ti γ and Ti δ subunits that form heterodimers which form a binding site for antigen and MHC through interaction of their variable domains. Furthermore, there is now direct evidence to show that at least in the case of one nominal antigen which is a hapten, there is a subsite on the Ti molecule which directly binds hapten in the absence of MHC with an affinity constant of ~$10^{-5}$ [Siliciano, R. F. et al., Cell 47: 161–171 (1996)].

Each Ti α and β subunit contains two extracellular domains, created by intrachain disulfide bonding of cysteine residues and a carboxy terminal hydrophobic transmembrane region followed by 5–6 amino acid cytoplasmic tails. The genes encoding the T cell receptor are assembled from separate gene segments, one of which encodes an invariant carboxy terminal constant region, while two or three other segments (V, D and J) encode the variable region of the molecule which recognizes antigen and MHC. Within the variable region are three regions of hypervariability that form the antigen binding pocket.

The organization of the gene locus which encodes the Ti β subunit consists of two tandemly arrayed sets of segments termed Dβ1-Jβ1-Cβ1 and Dβ2-Jβ2-Cβ2 and a set of 5' V genes. The two constant regions of the Ti β protein differ from each other by only six amino acids in the translated region. Located 5' to each Cβ region is a cluster of six functional J segments. Approximately 50 Vβ genes are known to exist in humans within the Ti β locus on chromosome 7 at 7q35. The Vα gene pool may be somewhat larger than Vβ, ~100 separated V genes. Furthermore, the organization of the Ti α locus is distinct from Ti β as it contains only a single constant region gene and multiple Jα segments (>25) dispersed over more than 60 Kb [Wilson, R. K. et al., Immunol. Rev. 101, 149 (1988)]. The Ti γ and Ti δ subunits are similar in structure to the Ti and Ti β subunits. Brenner, M. B. et al., Nature 322; 145–149 (1986).

Because of the obligatory association of Ti subunits with CD3 subunits in the endoplasmic reticulum prior to surface T cell receptor expression, genetic analysis and engineering of T cell receptors in secreted form has, to the present time, been impractical. Furthermore, the present inventors have observed that truncated forms of Ti α and Ti β subunits lacking transmembrane and intracytoplasmic segments have failed to coassociate and/or be secreted when expressed in eukaryotic systems, including CHO, baculovirus-SF9 and yeast.

SUMMARY OF THE INVENTION

The present invention circumvents these and other problems in the art.

The present invention concerns a soluble, single chain T cell receptor. Preferably, the soluble, single chain T cell receptor is a Ti β subunit fragment joined to a Ti α subunit fragment or a Ti γ subunit fragment joined to a Ti δ subunit fragment by an amino acid linker. Additionally preferred is a soluble, single chain T cell receptor that is biologically active.

The present invention further concerns a nucleic acid molecule comprising a nucleic acid sequence coding for a soluble, single chain T cell receptor. Preferably, the soluble, single chain T cell receptor is a Ti β subunit fragment joined to a Ti α subunit fragment or a Ti γ subunit fragment joined to a Ti δ subunit fragment by an amino acid linker. It is also preferred that the nucleic acid molecule is a DNA molecule, and the nucleic acid sequence is a DNA Sequence.

The present invention additionally concerns an expression vector containing a DNA sequence coding for a soluble, single chain T cell receptor. Preferably, the soluble, single chain T cell receptor is a Ti β subunit fragment joined to a Ti α subunit fragment or a Ti γ subunit fragment joined to a Ti δ subunit fragment by an amino acid linker.

The present invention also concerns prokaryotic or eukaryotic host cells containing an expression vector which contains a DNA sequence coding for a soluble, single chain T cell receptor. Preferably, the soluble, single chain T cell receptor is a Ti β subunit fragment joined to a Ti α subunit fragment or a Ti γ subunit fragment joined to a Ti δ subunit fragment by an amino acid linker.

BRIEF DESCRIPTION OF THE DRAWINGS

FIG. 2B shows the nucleotide sequence and deduced amino acid sequence of FL-specific scTCR.

DETAILED DESCRIPTION OF THE INVENTION

Figure 1:
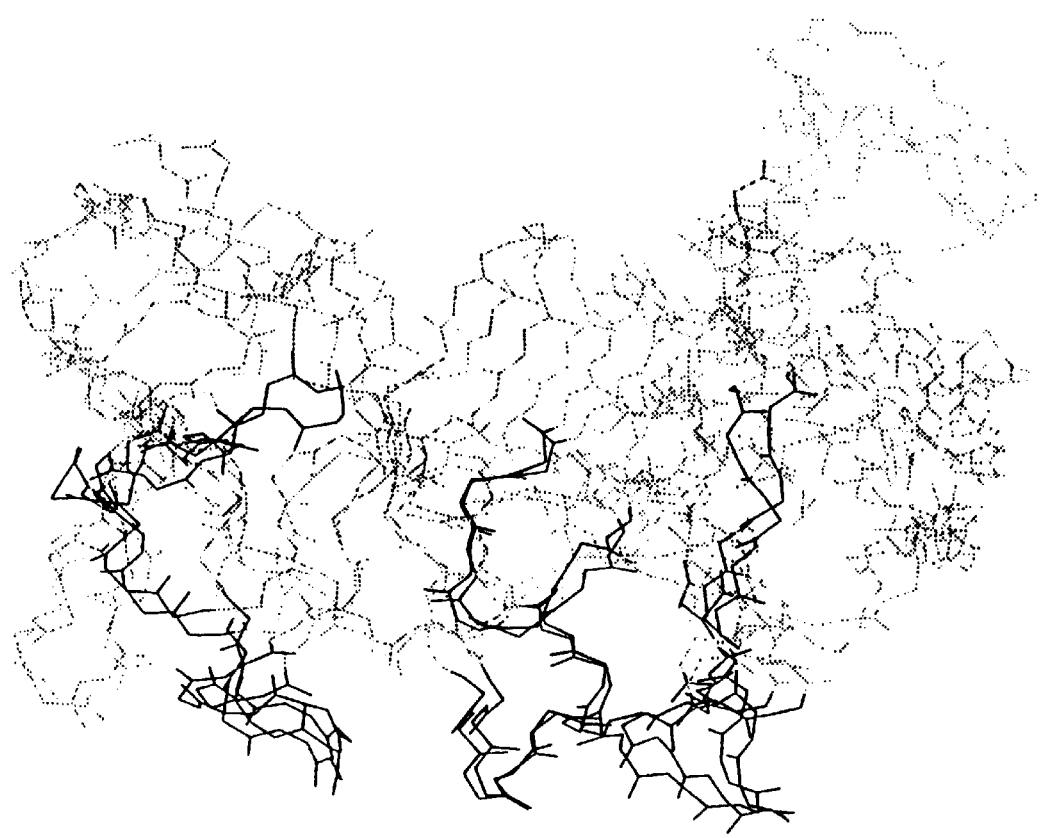
FIG. 1 shows a computer generated model of a single chain T cell receptor.

The present invention concerns a soluble, single chain T cell receptor. Preferably, the soluble, single chain T cell receptor is a Ti β subunit fragment joined to a Ti α subunit fragment or a Ti γ subunit fragment joined to a Ti δ subunit fragment by an amino acid linker. Also preferred is a single chain construct in which the carboxy terminus of the Ti β subunit fragment is joined by the amino acid linker to the amino terminus of the Ti subunit fragment. It is additionally preferred that the soluble, single chain T cell receptor be biologically active. That is, the biologically active, soluble, single chain T cell receptor of the present invention binds at least one antigen which is bound by a T cell receptor present on the surface of a T lymphocyte of mammalian origin. Typically, the biologically active, soluble, single chain T cell receptor is capable of binding the antigen or antigens it would bind as a component of a complete T cell receptor, either alone or in the context of a particular major histocompatability molecule. However, biologically inactive single chain T cell receptors also have value, for example, as immunogens to initiate in a mammalian host an immune response against a particular T cell subtype. It is further preferred that the soluble, single chain T cell receptor be soluble in aqueous solution.

As used in the present application, the term "fragment", when referring to polypeptide molecules or DNA sequences, means a portion of the referred to polypeptide molecule or DNA sequence.

All amino acid residues identified herein are in the natural L-configuration. In keeping with standard polypeptide nomenclature, J. Biol. Chem., 243:3557–59 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

As noted above, the soluble, single chain T cell receptors of the present invention contain portions of the Ti α and β or Ti γ and Ti δ subunits (sometimes collectively referred to hereinafter as Ti subunits). Any portions of the Ti subunits may be employed in the single chain construct as long as the portions used lack the transmembrane region of the corresponding intact Ti subunit, and contain those amino acids which are responsible for forming the antigen binding site. At a minimum, the complimentarity determining regions (CDRS) of the Ti subunits must be employed. It is preferred that the Ti α and Ti β or Ti γ and Ti δ subunit fragments employed correspond to the entire variable regions of the intact Ti subunits. In this case, it has been shown that the joined Ti and Ti β subunit fragments are biologically active and soluble in aqueous solution.

The present invention includes soluble, single chain T cell receptors in which the portions of the subunit fragments used are unmodified (i.e., the sequence used is the same as is present in the corresponding naturally occurring T cell receptor subunit), modified (i.e., the sequence of the naturally occurring T cell receptor subunit has been changed by the deletion, addition or substitution of at least one amino acid residue, for example, by replacing one or more hydrophobic amino acid residues with hydrophilic amino acid residues), or a combination of modified and unmodified subunit fragments.

As noted above, it is required that the single chain T cell receptor be soluble. By this, it is meant that the single chain T cell receptor must be soluble in an aqueous system. This solubility is conferred in part by removal of the transmembrane region of the corresponding intact Ti subunit. It is preferred that the single chain T cell receptor be soluble in a completely aqueous solution, and particularly in physiological buffers, although small amounts of solubility enhancers such as detergents and organic solvents may be employed for certain applications (e.g., in vitro diagnostic applications).

The identity of the amino acids in the amino acid linker used to join the Ti subunit fragments is not critical. It is only necessary that the linker be capable of permitting the joined Ti subunit fragments to associate in such a manner so as to form the antigen binding site. However, amino acids which inpart flexibility and aqueous solubility are most desirable. Among amino acids which impart flexibility, glycine, stands apart as the most effective due to its lack of β-carbons. Amino acids which increase aqueous solubility include, for example, serine, glutamine, aspartic acid, arginine and the like. Similarly, the length of the linker should be such as to allow the joined Ti subunit fragments to associate in such a manner so as to form the antigen binding site. The amino acid linker typically ranges from about 10 to about 30 amino acids in length, and is preferably about 15 to about 25 amino acids in length. A particularly preferred amino acid linker is one with the following sequence:

Pro-Gly-Gly-Gly-Gly-Ser-Gly-Gly-Gly-Gly-Ser-Gly-Gly-Gly-Gly-Ser-Gly-Gly-Gly-Gly-Ser-Gly-Ala.

In designing an appropriate amino acid linker, computer modeling may be employed. For example, an appropriate single chain T cell receptor model may be constructed in two stages as follows. First, using the "Homology" module of the INSIGHT software (Biosym Technologies Inc., San Diego, Calif.) running on the Iris 4D/80GT workstation (Silicon Graphics, Mountain View, Calif.), the single chain T cell receptor framework may be constructed using the atomic coordinates of the immunoglobulin $V_L$-$V_L$ dimer as a three-dimensional template, and an optimal amino acid sequence alignment between the T cell receptor variable- and variable-β domains and the $V_L$ immunoglobin domain as the starting point of the construction. The six "hypervariable" loops that form the antigen combining site may be approximated by implanting same-length loops, found in the Brookhaven Protein Databank, onto the constructed framework. The structure of the linker may then be similarly approximated. The crude model may then be subjected to energy minimization and 53 pseconds of dynamical simulation using the program CONGEN, which is derived from the program CHARM (See, Brook, B. et al., Journal of Computational chemistry 4, 187–217 (1983): Bruccoleri, R. and Karplus, M., Biopolymers 26, 136–168 (1987)). This protocol alleviates atomic overlaps and improves the stereochemistry of the model. An illustration depicting this model is shown in FIG. 1.

The amino acid linker may also be designed to meet a number of different needs apart from functioning as a linker. For example, monoclonal or polyclonal antibodies raised against the linker sequence may be capable of recognizing other single chain T cell receptors which contain this peptide sequence, even when the Ti subunit domains are distinct. Such a universal antibody reagent could be used in the purification of many different T cell receptor structures using immunoaffinity procedures.

The soluble, single chain T cell receptors of the present invention may be produced using various methods. For example, they may be obtained by synthetic means, i.e., chemical synthesis of the polypeptide from its component amino acids, by methods known to those of ordinary skill in the art. For example, the solid phase procedure described by Houghton et al., *Proc. Natl. Acad. Sci.* 82:5135 (1985) may be employed. It is preferred that the soluble, single chain T cell receptors be obtained by production in prokaryotic or eukaryotic host cells expressing a DNA sequence coding for the single chain T cell receptors as described herein, or by in vitro translation of the mRNA encoded by the DNA sequence coding for the single chain T cell receptors.

The soluble, single chain T cell receptors of the present invention may also be produced through chemical coupling procedures. For example, the Ti subunit fragments and the amino acid linker described above may be produced by synthetic chemical procedures or by recombinant DNA procedures. The various polypeptides may then be chemically coupled to produce the desired soluble, single chain T cell receptor. Various chemical coupling procedures known in the art may be used for this purpose. For example, carbodimide coupling, various active ester methods and enzyme-catalyzed bond formation may be employed.

The soluble, single chain T cell receptors may be isolated and purified to the degree desired using various protein purification techniques. For example, chromatographic procedures such as reverse phase high performance liquid chromatography, ion exchange chromatography, gel filtration chromatography and immunoaffinity chromatography may be employed.

The present invention also contemplates derivatives of the soluble, single chain T cell receptors. Such derivatives include, for example, single chain T cell receptors labeled with radio-isotopes such $^{125}$I, $^{131}$I, $^{14}$C, $^{35}$S, $^{3}$H, $^{112}$In, $^{99m}$Tc and the like, for in vitro or in vivo diagnostic purposes. Other derivatives contemplated by the present invention include, for example, soluble, single chain T cell receptors conjugated with a toxin, such as ricin or deglycosylated ricin A chain, for therapeutic purposes. Such derivatives may be prepared using methods known in the art.

It should be understood that the methodology described herein can be used to prepare soluble, single chain T cell receptors derived from animal species other than humans, and soluble, single chain T cell receptors for a wide variety of different antigens, for example, fluorescein, foreign major histocompatability molecules (MHC) and peptide antigens in the context of MHC molecules. These variations are included within the scope of the present invention.

The soluble, single chain T cell receptors of the present invention may be used in various ways. For example, radiolabeled single chain T cell receptors may be used as probes to identify antigen/MHC complex in vivo, including those responsible for autoimmune diseases. Furthermore, soluble, single chain T cell receptors can be used to bind specific antigen/MHC complexes on antigen presenting cells in vivo and hence prevent activation of autoreactive T cell clones by preventing their interaction with antigen/MHC. In this regard, soluble, single chain T cell receptors might be critical as competitive antagonists of the transmembrane CD3-Ti complex on these autoreactive cells. An advantage of this apparatus over anti-clonotypic antibodies is that soluble, single chain T cell receptors will bind to antigen/MHC potentially seen by a variety of autoreactive CD3-Ti complexes including the non-autologous clonotype. The soluble, single chain T cell receptors of the present invention can also be used to abrogate the immune response in infectious diseases, for example, chronic hepatitis. As an immunogen, the soluble, single chain T cell receptor may initiate an antiidiotypic response that could regulate responses of T cell clones expressing a related T cell receptor structure. The single chain constructs of the present invention can also be used to provide structural information about the nature of T cell receptor antigen/MHC binding regions and the relationship of immunoglobulin and T cell receptor CDRS. Macro-molecular modeling and crystallography in conjunction with in vitro functional studies of human T cell clones and in vivo studies in murine model systems may be used as a basis for rational drug design programs aimed at development of small molecules which abrogate T cell receptor-antigen interactions.

In using the soluble, single chain T cell receptors of the present invention to suppress autoimmune disease, the soluble, single chain T cell receptors may be administered parenterally to various mammalian species known to be subject to such maladies, e.g., humans, cats, dogs and the like, in a therapeutically effective amount within the dosage range of about 0.01 to 1.0 mg/kg/day, preferably about 0.1 to 1.0 mg/kg/day, on a regimen in single or 2 to 4 divided daily doses. Alternatively, the parenteral solution may be continuously infused to administer these dosage amounts. The active substance should be utilized in a parenteral solution containing about 1.0 to about 10.0 mg per unit of dosage of the single chain T cell receptor. They may be formulated in a conventional manner along with other physiologically acceptable materials, such as preservatives and stabilizers as called for by accepted pharmaceutical practice.

The present invention further concerns a nucleic acid molecule comprising a nucleic acid sequence coding for a soluble, single chain T cell receptor. Preferably, the soluble, single chain T cell receptor is a Ti subunit fragment joined to a Ti β subunit fragment or a Ti γ subunit fragment joined to a Ti δ subunit fragment by an amino acid linker. It is also preferred that the nucleic acid molecule is a DNA molecule and the nucleic acid sequence is a DNA sequence, although RNA molecules and RNA sequences are also contemplated. Further preferred is a DNA sequence coding for a soluble, single chain T cell receptor wherein the Ti and Ti β or Ti γ and Ti δ subunit fragments employed correspond to the entire variable regions of the intact Ti and Ti β or Ti γ and Ti δ subunits, The DNA sequence of the present invention may be prepared in various ways, for example, through genetic engineering techniques. It is preferred that the DNA sequences coding for the appropriate Ti subunit fragments be prepared by polymerase chain reaction (PCR) using DNA sequences coding for the intact subunits as templates, the DNA sequence coding for the amino acid linker be prepared by chemical synthesis, and the various DNA sequences be ligated to form a DNA sequence coding for a single chain T cell receptor. The DNA sequences of the present invention may also be prepared through chemical synthesis using known methods.

The DNA sequences of the present invention coding for soluble, single chain T cell receptors may also be used to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These mutant DNA sequences may be prepared, for example, by mutating the soluble, single chain T cell receptor DNA sequence so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–8764 (1985) and Kunkel, T. A., Proc. Natl. Acad. Sci. USA 82: 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in practicing the present invention. For example, these mutations may provide sites for cleavage by restriction endonucleases, permit higher levels of production, easier purification, greater solubility or higher biological activity. For example, for a single chain T cell receptor derived from the variable and β domains of an anti-fluorescein T cell receptor (FIG. 2A, FIG. 2B), computer modeling studies indicate that the hydrophobic amino acid residues Phe 10, Met 41, Leu 111, Ile 146, Ile 152, Phe 173 and Ile 245 all cluster on the bottom part of the single chain construct, distal from the antigen-combining site. Other hydrophobic amino acids which can be mutated include Leu 22, Phe 74, and Met 212. Some of these amino acids may mediate non-covalent interactions between the variable and constant domains of the intact T cell receptor. In the shortened single chain T cell receptor, however, solvent exposure of these positions may lead to decreased solubility of the constructed protein. By mutating the DNA sequences encoding these amino acid residues to DNA sequences that code for amino acid residues with more polar side chains, the aqueous solubility of the encoded single chain T cell receptor can be increased. All such variant DNA molecules and polypeptide molecules are included within the scope of the present invention.

The present invention also concerns expression vectors containing a DNA sequence coding for a soluble, single chain T cell receptor. Preferably, the soluble, single chain T cell receptor is a Ti subunit fragment joined to a Ti β subunit fragment or a Ti γ subunit fragment joined to a Ti δ subunit fragment by an amino acid linker. Further preferred are expression vectors containing one or more control DNA sequences operatively linked to the DNA sequence coding for a soluble, single chain T cell receptor. As used in this context, the term "operatively linked" means that the control DNA sequences are capable of directing the replication and/or the expression of the DNA sequence coding for the soluble, single chain T cell receptor. Also preferred are expression vectors (and the corresponding host cells) wherein the soluble, single chain T cell receptor has been modified by replacing one or more hydrophobic amino acid residues with hydrophilic amino acid residues.

Expression vectors of utility in the present invention are often in the form of "plasmids", which refer to circular double stranded DNA loops which, in their vector form, are not bound to the chromosome. However, the present invention is intended to include such other forms of expression vectors which serve equivalent functions and which become known in the art subsequently hereto.

Expression vectors useful in the present invention typically contain an origin of replication, a promoter located in front of (i.e., upstream of) the qene to be expressed, the gene to be expressed, replication termination sequences and the remaining vector. The expression vectors may also include other DNA sequences known in the art, for example, stability leader sequences which provide for stability of the expression product, regulatory sequences which allow expression of the structural gene to be modulated (e.g., by the presence or absence of nutrients in the growth medium), marking sequences which are capable of providing phenotypic selection in transformed host cells, and sequences which. provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionien promoter), or from viruses that grow in these cells (e.g., vaccinia virus 7.5 K promoter). An expression vector as contemplated by the present invention is at least capable of directing the replication, and preferably the expression, of the DNA sequences of the present invention coding for soluble, single chain T cell receptors. Suitable expression vectors into which the DNA sequences of the present invention may be inserted are commercially available, and include, for example, pUC19 and derivatives thereof, such as pBluescript SIC (+/−) (Stratagene, La Jolla, Calif.), and pBR322 and derivatives thereof, such as pIN-I, pIN-II, pIN-III, pIN-III-ompA1 and pIN-III($1pp^{P-}$) [See, Duffaud, G. D. et. al., In: Methods in Enzymology, Vol. 153, p. 492 (1987)].

Particularly useful as expression vectors are those derived from the secretion vector pPL2.

The expression vectors of the present invention may be constructed using standard recombinant DNA techniques known in the art, many of which are described in Maniatis et al., *Molecular Cloning: A Laboratory Manual,* Cold Spring Harbor Laboratory, Cold Spring Harbor, N.Y. (1982).

The present invention additionally concerns host cells containing an expression vector which contains a DNA sequence coding for a soluble, single chain T cell receptor. Preferably, the soluble, single chain T cell receptor is a Ti subunit fragment joined to a Ti β subunit or a Ti γ subunit fragment joined to a Ti δ subunit fragment by an amino acid liner. Additionally preferred are host cells containing an expression vector comprising one or more control DNA sequence capable of directing the replication and/or the expression of and operatively linked to a DNA sequence coding for a soluble, single chain T cell receptor. Suitable host cells include both prokaryotic and eukaryotic cells. Suitable prokaryotic host cells include, for example, bacterial cells. Suitable eukaryotic host cells include, for example, CHO cells.

Preferred as host cells are bacterial cells such as *Escherichia coli* cells. A particularly preferred host cell is *E. coli* strain Mc1000.

The expression vectors of the present invention may be introduced into host cells by various methods known in the art. For example, transfection of host cells with expression vectors may be carried out by the calcium phosphate precipitation method. However, other methods for introducing expression vectors into host cells, for example, electroporation, nuclear injection or protoplast fusion, may also be employed.

Once an expression vector has been introduced into an appropriate host cell, the host cell may be cultured under conditions permitting expression of large amounts of soluble, single chain T cell receptors.

Host cells containing an expression vector which contains a DNA sequence coding for a soluble, single chain T cell receptor may be identified by one or more of the following four general approaches: (a) DNA-DNA hybridization; (b) the presence or absence of "marker" gene functions; (c) assessing the level of transcription as measured by the production of mRNA transcripts in the host cell; and (d) detection of the gene product immunologically and/or by its biological activity.

In the first approach, the presence of a DNA sequence coding for a soluble, singe chain T cell receptor can be detected by DNA-DNA hybridization using probes complementary to the DNA sequence.

In the second approach, the recombinant expression vector host system can be identified and selected based upon the presence or absence of certain "marker" gene functions (e.g., thymidine kinase activity, resistance to antibiotics, etc.). For example, if a DNA sequence coding for a soluble, single chain T cell receptor is inserted within a marker gene sequence of the expression vector, recombinants containing the DNA sequence coding for the single chain T cell receptor can be identified by the absence of the marker gene function. Alternatively, a marker gene can be placed in tandem with the DNA sequence coding for a soluble, single chain T cell receptor under the control of the same or a different promoter used to control the soluble, single chain T cell receptor coding sequence. Expression of the marker in response to induction or selection indicates expression of the DNA sequence coding for the soluble, single chain T cell receptor.

In the third approach, the production of soluble, single chain T cell receptor mRNA transcripts can be assessed by hybridization assays. For example, polyadenylated RNA can be isolated and analyzed by Northern blotting using a probe complementary to the RNA sequence. Alternatively, the total nucleic acids of the host cell may be extracted and assayed for hybridization to such probes.

In the fourth approach, the expression of a soluble, single chain T cell receptor can be assessed immunologically, for example, by Western blotting, or by the detection of biologically active gene product. Where the host cell secretes the gene product, the cell free media obtained from the cultured transfected host cells may be assayed for antigen binding activity. Where the gene product is not secreted, cell lysates may be assayed for such activity.

The soluble, single chain T cell receptor may then be isolated and purified using various techniques as described herein.

The DNA sequences of expression vectors, plasmids or DNA molecules of the presence invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA control sequences will function equally well to express the DNA sequences of the present invention. Neither will all host cells function equally well with the same expression system. However, one skilled in the art may make a selection among expression vectors, DNA control sequences, and host cells using the guidance provided herein without undue experimentation and without departing from the scope of the present invention.

The following examples are further illustrative of the present invention. These examples are not intended to limit the scope of the present invention, and provide further understanding of the invention.

EXAMPLE I

Production of Soluble Anti-Fluorescein Single Chain T Cell Receptor

A. Materials

All chemicals were purchased from Sigma Chemical Co. (St. Louis, Mo.) unless otherwise noted. Oligonucleotides were prepared on a Model 381A DNA Synthesizer (Applied Biosystems, Foster City, Calif.) unless otherwise noted. Enzymes were purchased from and used as suggested by New England Biolabs (Beverly, Mass.) unless otherwise noted. The $E.\ coli$ strains utilized include: MZ13B [F-$\Delta$lac-X174 $\Delta$(brnQ phoB) tsx trp(am) rpsL(str$^r$]; KS265 [$\Delta$lac-X74 glaE glaK rpsL(str$^r$) $\Delta$phoA(PvuII) ara$\Delta$139 phoR]; Mc1000 [F-araD139 $\Delta$(ara-leu) 7697 $\Delta$lac-74 galU galK rpsL].

B. Cloning of Fluorescein-Specific T Cell Receptor

Fluorescein (FL)-specific T cell clones were obtained as described in Siliciano, R. F. et al., Cell 47: 161–171 (1986). Briefly, fluorescein-specific T cell clones were generated by stimulating human peripheral blood T lymphocytes with irradiated autologous mononuclear cells that had been covalently coupled with fluorescein-5-isothiocyanate (FITC). After repetitive stimulation, nominal antigen binding cells were further enriched by fluorescence activated cell sorting of T lymphocytes capable of efficiently binding an FITC-conjugated polymer. Both CD4+,CD8– and CD8+, CD4– clones were subsequently obtained and proliferation assays determined that they were MHC class II and MHC class I restricted, respectively. Importantly, when high levels of the nominal antigen were expressed on the antigen presenting cell (APC) as was achieved by direct coupling of APC with high concentrations of FITC, MHC restriction could be overcome. This relative MHC independence was substantiated by three independent observations. First, anti-class I antibodies could not block the cytolysis of highly FITC-labeled target cells. Second, the binding of multivalent, FITC-coupled polymers to the clones could be specifically blocked by soluble monovalent antigen. Third, the $\alpha$-$\beta$ T cell receptor heterodimer could be specifically depleted from lysates of the FL-specific clones via FITC-coupled affinity columns.

One of these CD4+,CD8– clones (RFL3.8) was chosen for further analysis and a cDNA library was constructed in $\lambda$gt10 (See, Maniatis et al., supra). This library was screened as described in Maniatis et al., supra with probes derived from the constant regions of the human $\alpha$ and $\beta$ chains of the T cell receptor [See, Davis, M. M. et al., Nature 334, 395–402 (1988)] from REX, a Jurkat variant, and labeled by the random priming method, and positive clones encoding Ti $\beta$ and Ti $\alpha$ subunits obtained. The complete nucleotide sequences of the FL-specific TCR $\alpha$ and $\beta$ variable regions were determined after subcloning the full length Eco RI Ti and Ti $\beta$ cDNA inserts into pUC18 (pTCRV and pTCRV$\beta$, respectively) by the dideoxy chain termination method on both strands as described in Sanger, F. et al., supra. Analysis of the $\beta$ chain cDNA sequence demonstrated that it contained V$\beta$13.2, D$\beta$1.5 and C$\beta$1 germline elements whereas the a chain cDNA sequence contained a previously uncharacterized V$\alpha$ and the J$\alpha$F element.

C. Construction of DNA Sequence Encoding Single Chain T Cell Receptor

In order to produce single chain T cell receptors (scTCR's), the following strategy was employed. Polymerase chain reaction (PCR) [(See, Saiki, R. K. et al., Science 230, 1350–1354 (1985); Saiki, R. K. et al., Science 239, 487–491 (1988); Kumar, R., Technique 1, 133–152 (1989)] was used to introduce unique restriction sites at the ends of the cDNA regions encoding the variable domains of the Ti α and Ti β chains. Corresponding restriction sites were placed at the ends of a linker designed to link the carboxy-terminus of the Ti β variable domain to the amino-terminus of the Ti variable domain. The amino acid sequence of the linker was chosen via computer modeling studies based on the assumption that the gross features of the variable domains of the T cell receptor would be similar to the known crystal-lographic structure of immunoglobulin variable domains. The linker was designed to incorporate a sufficient number of residues to bridge the two variable domains yet be flexible and thus impose no restriction on domain folding.

More specifically, a 756 bp DNA segment encoding the variable region sequences of the α and β chains of the T cell receptor connected via a synthetic linker sequence was assembled from three pieces as follows.

The β chain variable region was obtained as an Eco RI and Ava I fragment from a cDNA for the β chain (in plasmid pTCRVβ) by PCR using the following two primers:
5' primer: 5'-GGGCCCGAATTCATGAATGCTGGTGTC ACTCAGACC-3'
3' primer: 5'-GATCTGCCCGGGTAGGATGGAGAG TCGAGTCCC-3'

This 363 bp fragment had Eco RI (underlined in 5' primer) and Ava I (underlined in 3' primer) restriction sites.

The chain variable region was obtained by PCR amplification of a cDNA clone contained in plasmid pTCRV using the following two primers:
3' primer: 5'-GGGCCCAGCTGTCATTATGCAATCAC AGAAAGTCTTGTGCC-3'
5' primer: 5'-CCCGGGGCGCCCAGCAGCAGGTG AAACAAAGTCCT-3'

This 348 bp long fragment had Nar I (underlined in 5' primer) and Pvu II (underlined in 3' primer) restriction sites.

In both cases, PCR was carried out essentially as suggested by the Gene-Amp kit's manufacturer (Perkin-Elmer/Cetus, Norwalk, Conn.). Amplification consisted of 30 cycles. Each cycle consisted of melting at 94° C. for 1 minute, annealing at 50° C. for 2 minutes and polymerizing at 72° C. for 3 minutes. The polymerization time at 72° C. was extended by 5 seconds after each cycle. In each PCR reaction mixture, 0.5 μg of plasmid DNA containing the cDNA insert for the (pTCRV) or the β (pTCRVβ) chains was used. All reactions were in a 200 μl volume and included 5 units of Taq polymerase (Perkin-Elmer Cetus). The PCR products were cleaved by the appropriate restriction enzymes (Nar I for Vα and Ava I for Vβ) and gel purified as described in Ausubel, F. M. et al., eds., Current Protocols in Molecular Biology, John Wily & Sons, N.Y. (1987) on a 4% native polyacrylamide gel run in 1×Tris/borate/EDTA (TBE) buffer.

Two complementary oligonucleotides encoding a 61 bp linker designed to have restriction half-sites for AvaI for NarI at its termini were synthesized. Their sequences were as follows:
Sense oligonucleotide:
5'-CCGGGGGCGGTGGTTCTGGTGGTGGTGGTGGTT CTGGTGGTGGTGGTTCTGGTGGTGGTGGTTC TGG-3'

Antisense oligonucleotide:
5'-CGCCAGAACCACCACCACCAGAACAACCACCA CCACCAGAACCACCACCACCACCAGAACCACCG CCC-3'

Restriction enzyme cohesive termini are underlined (in sense oligonucleotide, Ava I half-site at 5' end and Nar I half-site at 3' end; in antisense oligonucleotide, Nar I half-site at 5' end and Ava I half-site at 3' end). These oligonucleotides as well as the PCR primers described above were synthesized utilizing a Model 380B DNA synthesizer (Applied Biosystems) using β-cyanoethyl chemistry as recommended by the manufacturer. The oligonucleotides were hybridized to each other by mixing approximately 0.1 μg of each oligonucleotide in a 100 μl volume containing 10 mM Tris.HCl, pH 7.4, and 1 mM $MgCl_2$. The mixture was covered with 3 drops of paraffin oil to prevent evaporation and heated in a boiling water bath for 10 minutes. The hybrids were slowly annealed by cooling to room temperature overnight.

The purified PCR products and linker were ligated at a ratio of 1:10, respectively. Ligation was carried out in a 50 μl reaction mixture using T4 ligase and buffer from Bethesda Research Labs (Gaithersburg, Md.) for 16 hours at 16° C. The DNA ligase in the reaction mixture was inactivated by heating to 65° C. for 20 minutes. The ligation reaction was diluted to 200 μl in restriction digestion buffer (New England Biolabs) and Eco RI and Pvu II (50 units each) were added. Digestion was carried out at 37° C. for 6 hours. Digested chimeric DNA fragments were purified by gel electrophoresis using a 4% polyacrylamide gel run in 1×TBE, and the DNA visualized by ethidium bromide staining and UV light. The DNA was excised from the gel and recovered by the "crush and soak" procedure (See, Maniatis et al., supra).

Figure 3:
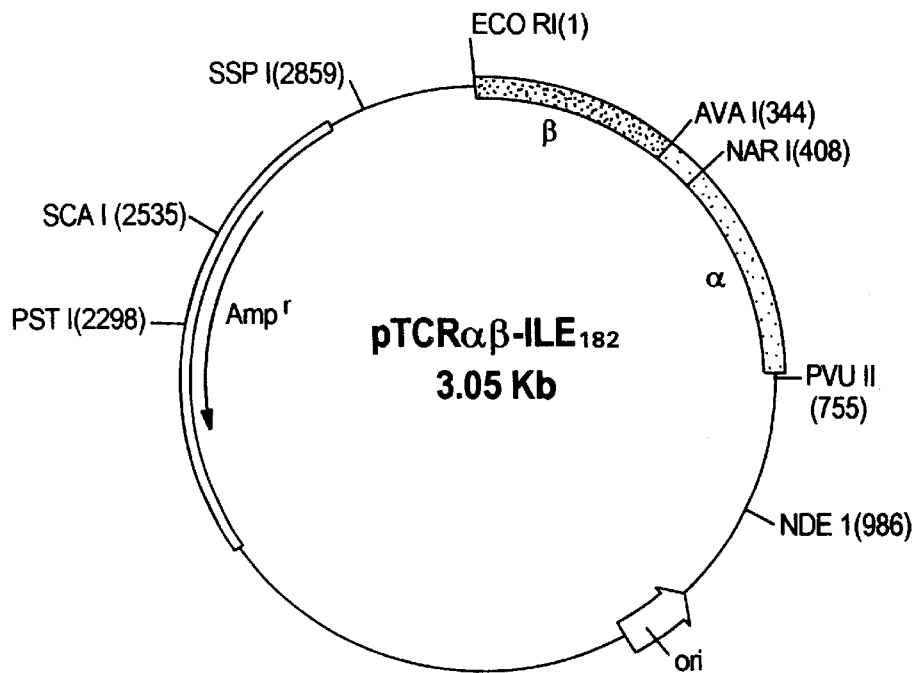
FIG. 3 shows maps of plasmids pTCR β-ILE$_{182}$ and pTCR β-MET$_{182}$.
Figure 3:
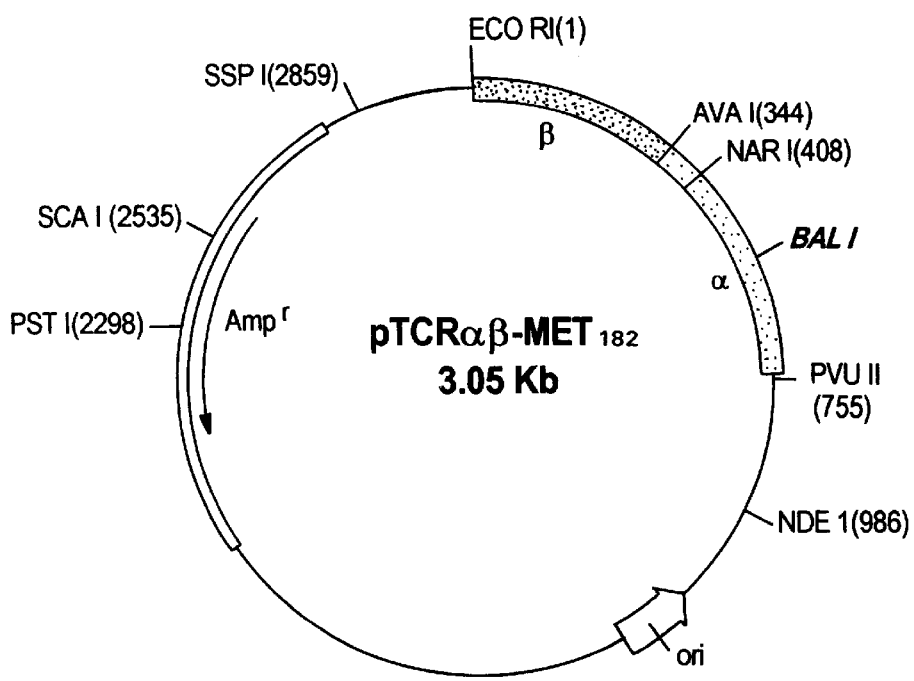
Figure 4:
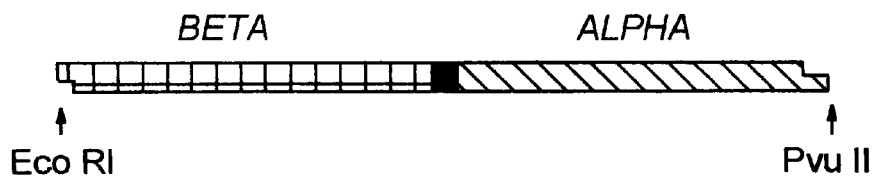
FIG. 4 shows scale drawings depicting single chain T cell receptor encoding DNA fragments.
Figure 4:
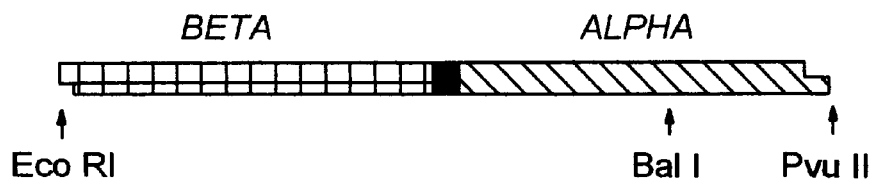

The chimeric fragment was then cloned into plasmid pBR322 cleaved with Pvu II and Eco RI. 1 μg of pBR322 DNA was digested to completion with Eco RI and Pvu II (New England Biolabs) as recommended by the manufacturer. A 2.3 kb vector fragment was eluted after electrophoresis in a 1.0% agarose gel. 50 ng of the pBR322 derived vector was ligated with 200 ng of the chimeric single chain T cell receptor DNA fragment using T4 DNA ligase (Bethesda Research Labs) for 16 hours at 16° C. A portion (1/10) of the ligation reaction was used to transform competent E. Coli, strain DH5 (Bethesda Research Labs). Colonies were plated on agar containing 100 μg/ml ampicillin. Colonies were then replicated on agar plates containing ampicilin or tetracyclin. Recombinants (pBR containing the single chain T cell receptor fragment inserted between the Puv II and Eco RI sites) grew only on the ampicillin containing plates whereas the pBR322 vector grew on both ampicilin and tetracyclin containing plates. These clones were further tested by diagnostic restriction enzyme digestions. Three clones were selected for further analysis. The single chain T cell receptor inserts in each of these three clones were sequenced on both strands by the dideoxy chain termination method. Two clones, #2 and #5, were selected for expression studies and were designated pTCR #2 and pTCR #5, respectively. Maps of these plasmids are shown in FIG. 3 (PTCR #2=pTCR β-$ILE_{182}$; pTCR #5=pTCR β-$MET_{182}$). Both plasmids are approximately 3.0 kb in length. The recombinant receptor insert in these plasmids is schematically shown in FIG. 4. The DNA sequence of the two isolates were identical with one exception. Isolate #2 carries an A at nucleotide position 555, and as a consequence the 182nd codon, ATA, encodes an isoleucine residue. Isolate #5 carries a G at nucleotide position 555, and as a consequence the 182nd codon, ATG, encodes a methionine residue.

The nucleotide sequence and deduced amino acid sequence translation of the resulting scTCR construct (Isolate #2) is shown in FIG. 2B. Amino acids +1 to +111 comprise the variable β domain and amino acids +135 to +246 comprise the variable a domain. The linker residues (+112 to +134) are underlined. An ATG codon precedes the Asn+1 codon for purposes of expression in *E. coli* in the absence of a signal sequence. Note the Eco RI restriction site 5' to the ATG.

D. Construction of an Alkaline Phosphatase/scTCR Fusion Protein

Initially, the construct displayed in FIG. 1 and an antisense version were cloned into pKK233-2 and *E. coli* JM105 was transformed. Attempts were made to identify the expected product in total cell lysates subjected to sodium dodecyl sulphate-polyacrylamide gel electrophoresis (SDS-PAGE), but specific bands were not observed, presumably as a consequence of unsatisfactory levels of protein expression and/or degradation.

Figure 2A:
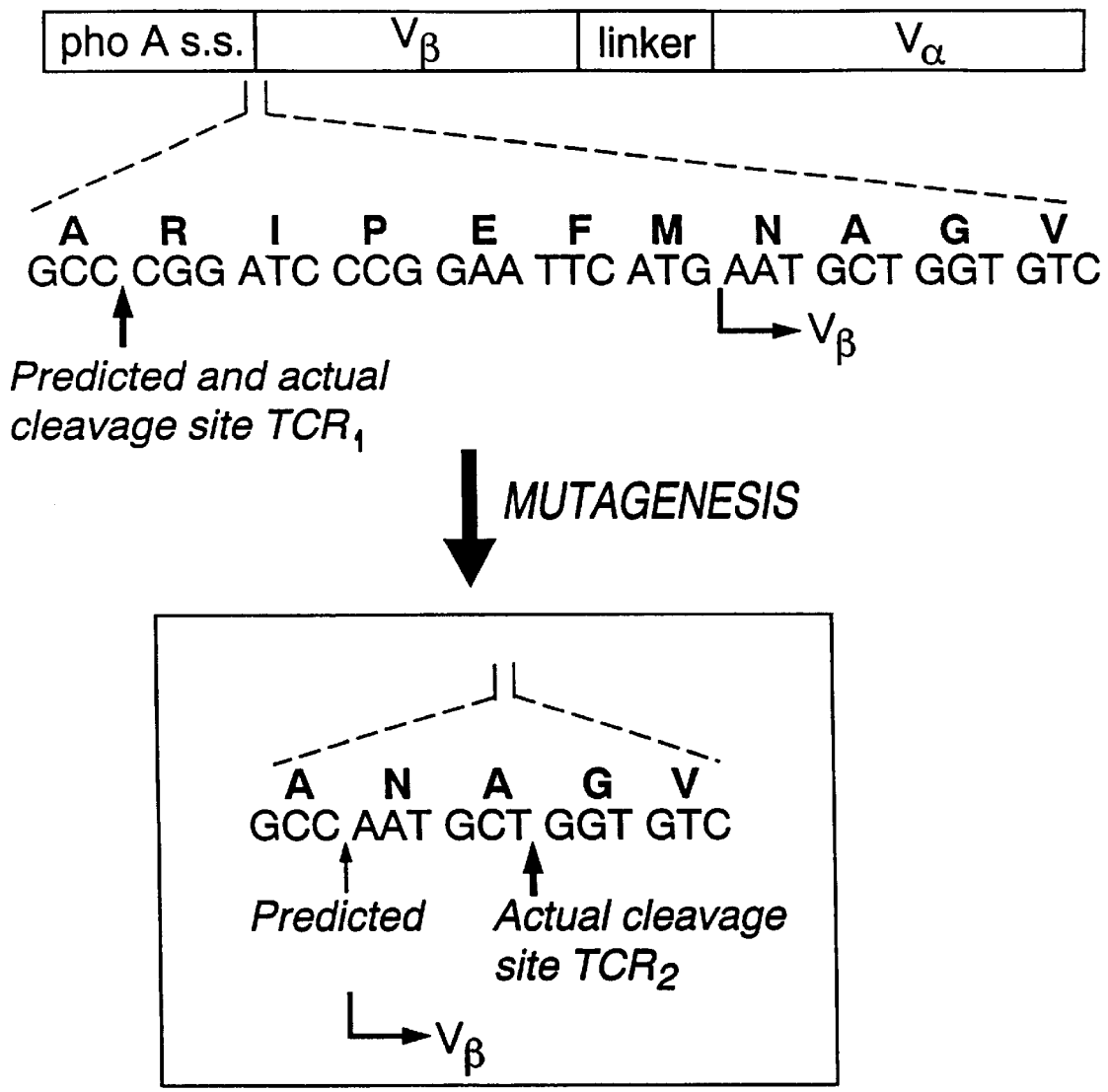
FIG. 2A shows a schematic diagram indicating the order of the TCR domains and peptide linker segments.

Subsequently, the scTCR construct was subcloned into a secretion vector, pFL2. This vector was chosen as it had been previously used to direct the secretion of foreign proteins into the periplasmic space of *E. coli*. The advantages of periplasmic secretion include a non-reducing environment which allows the formation Of disulfide bonds, and fewer contaminating *E. coli* proteins when periplasmic fractions alone are isolated. In order to use this system, the protein of interest may be fused downstream of the post-translationally cleaved leader sequence of a native or recombinant periplasmic protein. The pPL2 vector uses that of the alkaline phosphatase protein (phoA gene product). Subcloning the scTCR into pPL2 generated six additional residues at the predicted amino-terminus of the mature scTCR protein (FIG. 2A). These residues were later removed by site-directed mutagenesis.

The Eco RI/Pvu II fragment encoding the scTCR was inserted into the Xma I site of pPL2 (See, Li, P. et al., Proc. Natl. Acad. Sci. USA 85: 7685–7689 (1988)) by blunt-ending both the scTCR fragment and the pPL2 vector and then ligating to create pPL2/scTCR1 (See, Maniatis et al., supra). Six non-native amino acids that had been introduced at the fusion site during the construction were removed by site-directed mutagenesis using the Amersham kit according to the manufacturer's recommendations after subcloning a 3 Kb Kpn I fragment of the scTCR1 vector into m13 using standard procedures (See, Maniatis et al., supra). Double stranded sequencing was used to confirm the mutations and the 3 Kb Kpn I fragment was ligated using standard procedures to a 6 Kb Kpn I vector fragment to construct pPL2/scTCR2 lacking the six non-native residues. *E coli* strain MZ13b was used for all transformations during construction.

E. Expression of a scTCR in *E. coli*

The pPL2/scTCR 1 and 2 constructs were introduced into *E. coli* strain KS265 (phoA-, phoR-) by the calcium phosphate precipitation method for constitutive expression. The colony size of the *E. coli* transformed with the sense pPL2/scTCR was 5–10 fold smaller as compared to the same *E. coli* transformed by the antisense pPL2/scTCR. Total cell lysates of colonies containing the sense pPL2/scTCR1 or pPL2/scTCR2 streaked onto Luria broth (LB)-kanamycin plates demonstrated the presence of a putative scTCR product of ~30 KD on SDS-PAGE analysis. The growth of these colonies in liquid media, however, resulted in the loss of detectable expression. These results suggested that expression of the scTCR product was harmful to the *E. coli*, and mutants which prevented its expression were being selected for.

Strain KS265 is phoR- and therefore lacks the physiological negative regulator of the phoA promoter, allowing the scTCR to be constitutively expressed. In order to eliminate the toxic effects of the scTCR, the scTCR/pPL2 construct was introduced into a phoR+ strain, Mc1000 using the calcium phosphate precipitation method (See, Maniatis et al., supra). In this strain, expression of the scTCR was prevented until the negatove regulator was inactivated by subjecting late log phase *E. coli* to phosphate starvation, the physiological stimuli for transcription of the phoA gene.

Plasmid pPL2/scTCR2 in *Escherichia coli* strain Mc1000 was deposited with the American Type Culture Collection, Rockville, Md., on May 15, 1990 under the Budapest Treaty and assigned ATCC accession no. 68327.

To induce the expression of the scTCR, 40 ml of a fresh overnight culture of Mc1000 transformed with scTCR/pPL2 grown at 37° C. in Luria broth containing 30 μg/ml kanamycin sulfate was pelleted, washed with 10 ml of LP (low phosphate) medium (per liter: 8.4 g morpholine propane sulfonic acid (MOPS), 0.8 g tricine, 2.92 g NaCl, 13.6 mg $KH_2PO_4$, 1.6 g KOH, 0.51 g $NH_4Cl$, 1.072 g $MgCl_2.6H2O$, 0.64 μl concentrated HCl, 4 mg $FeCl_2.4H_2O$, 0.1472 g $CaCl_2.2H_2O$, 6.8 μg $H_3BO_3$, 3.2 μg $MnCl_2.4H_2O$, 1.44 μg $CoCl_2.H_2O$, 32 ng of 0.267 M $K_2SO_4$, 20 ml of 7.5% casamino acids, 20 ml of 20% glucose, 1 mg thiamine.HCl, and 30 mg kanamycin sulfate), resuspended in 4 liters of LP medium and aliquotted (8×500 ml) into 2 liter flasks. The cultures were grown at 37° C., with shaking at 250 rpm for 8.5 hours. Total cell lysates were analyzed by SDS-PAGE after heating the cell pellets in reducing sample buffer (per ml: 7.6 mg Tris base, 100 μl glycerol, 10 mg SDS, 10 μl beta-mercaptoethanol (BME), 0.5 mg bromophenol blue, adjusted to pH 6.8) at 100° C. for 5 minutes. Putative scTCR bands on such gels were confirmed by transferring the proteins to polyvinylidene difluoride (PVDF) membranes, visualizing bands via Coomassie staining and determining the amino acid sequence of cut out bands as described in Matsudaira, P., J. Biol. Chem. 262, 10035–10038 (1987) on an Applied Biosystems 470A protein sequencer. Approximately 100–250 pM of protein was utilized for sequencing purposes. A minimum of 10 cycles was obtained for each sequencing run.

Upon such induction, a specific band of ~30KD in total cell lysates of *E. coli* grown in liquid culture was detected. The apparent sizes of the TCR1 and TCR2 proteins were slightly larger than that predicted (25,896 KD for TCR2 for example), but their identity was confirmed by amino acid sequence analysis of the PVDF blotted band (FIG. 2A). The latter analysis confirmed that the phoA leader sequence had been cleaved from the TCR1 and TCR2 proteins. However, cleavage occurred two amino acids carboxy terminal to the predicted amino terminus in the case of TCR2, causing the amino terminus to begin Gly-Val-Thr rather than Asn-Ala-Gly-Val-Thr. Subsequent studies utilized TCR2 protein to avoid any adverse structural consequences of the 6 amino acid residues resulting from the fusion product.

F. Purification of scTCR

As amino acid sequencing had indicated that the phoA leader sequence had been cleaved from the scTCR, attempts were made to isolate the protein from the periplasmic space. However, the scTCR was always found to remain in low speed pellets. Neither salt washes nor non-denaturing detergents were able to solubilize the protein from these pellets. Surprisingly, an inclusion body purification was successfully employed. In this procedure, cells were pelleted (10,000 rpm, 10 minutes, Sorvall RC5B) at 4° C. and resuspended in 400 ml of 50 mM Tris-HCl (pH 7.5), 5 mM EDTA, 3 mg/ml lysozyme. After incubation on ice for 2 hours, 28 ml of 5 M NaCl and 30 ml of 10% Nonidet-P40 (NP40) were added. Incubation on ice was continued for 30 minutes followed by three 30 second pulses of sonication using a Branson 250 Sonifier. After centrifuging at 10,000 rpm for 10 minutes, the pellet was resuspended thoroughly in 50 ml of 10 mM Tris-HCl (pH 7.5), 1 mM EDTA, 0.5% NP40, 1 M NaCl and repelleted. The pellet was likewise washed again with the same buffer and then twice more with the same buffer without NaCl. It was then dissolved in 8 ml of freshly prepared and Sep-Pak'd (Accell QMA Cartridge, Millipore) 8 M urea. This solution was aliquotted and micro-centrifuged (Fisher) for 10 minutes. The supernatants were combined and flushed with $N_2$ gas. 80 $\mu$l of 1 M Tris-HCl (pH 8) and 24.7 mg of dithiothreitol were added. After incubating at room temperature for 30 minutes, 1 ml aliquots were diluted 1:1 in 0.1% trifluoroacetic acid (TFA)/$H_2O$ and loaded onto a C4-reverse phase high performance liquid chromatography (C4-RPHPLC) column (Vydac) attached to a Hewlet-Packard 1090 liquid chromatograph pumping at 1 ml/min with 0.1% TFA/$H_2O$. Fractions were collected during a 27–30% 0.1% TFA/acetonitrile 6 minute linear gradient. 5 $\mu$l of each fraction was dried down (Speed Vac Concentrator, Savant), resuspended in 10 $\mu$l reducing SDS-PAGE sample buffer, electrophoresed on a SDS-12.5% polyacrylamide gel as described in Laemmli, U. K., Nature 227, 680–685 (1970), and Coomassie blue stained. Fractions containing the mature scTCR were combined, solvent was evaporated (Speed Vac Concentrator) and the pellet was resuspended in freshly prepared 8 M urea at a concentration of approximately 2 mg/ml as estimated from the Coomassie blue stained gel.

Figure 5:
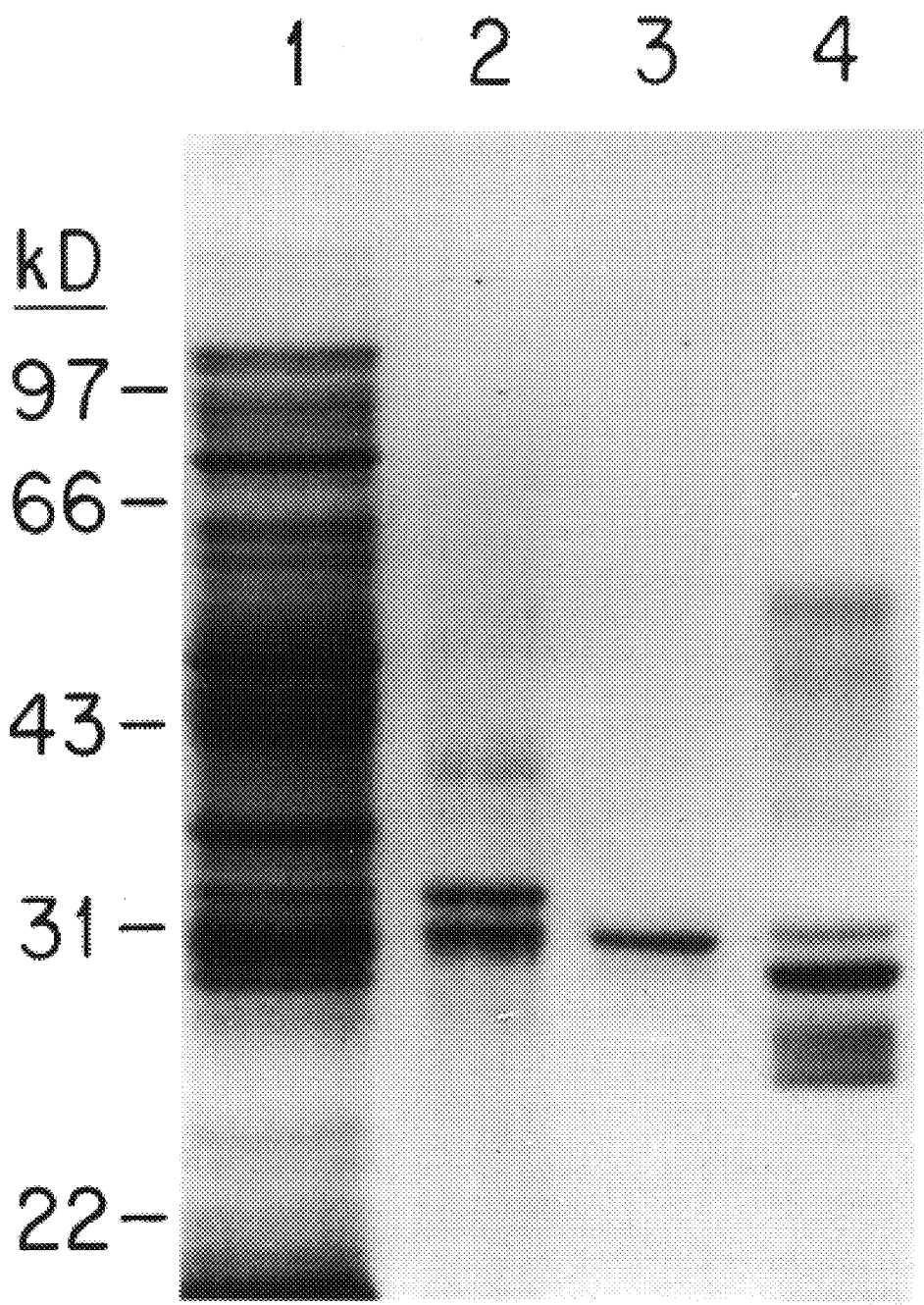
FIG. 5 shows the purification of a single chain T cell receptor.

This inclusion body purification protocol was found to achieve >40% purification (FIG. 5, lane 2). The major impurities of similar apparent molecular weight (32 KD and 29 KD) were identified by amino acid sequencing as the unprocessed scTCR and the kanamycin resistance gene product, respectively. Reverse phase HPLC was used to separate the impurities from the processed scTCR. This procedure resulted in material that was >95% pure, as judged by Coomassie blue stained gels (FIG. 5, lane 3).

The need for an inclusion body-type protocol suggested that the scTCR had formed insoluble aggregates after being translocated into the periplasm. Solubility studies were performed by rapidly diluting (1:100) the purified scTCR dissolved in 8 M urea into various buffers, incubating for 30 minutes, microcentrifuging and then analyzing the ratios of soluble vs. pelleted vs. tube-absorbed material by SDS-PAGE. These experiments demonstrated that the scTCR would remain soluble in buffers of low pH and ionic strength (eg., 10 mM sodium acetate, pH 5). Adding detergents to physiological buffers allowed the recovery of soluble material in this assay. Material solubilized in low pH buffers could be concentrated to greater than 1 mg/ml without precipitating, provided detergents (eg., 0.1% 3-[(3-cholamidopropyl)dimethylammonia]-propane-sulfonate; CHAPS) were added to prevent it from sticking to the Centricon 10 concentrating apparatus. Consequently, the scTCRs are routinely concentrated (and refolded) in 10 mM sodium acetate (pH 5) containing 0.1% CHAPS.

G. Refolding of scTCR

The purified scTCR in 8 M urea was rapidly diluted 1:100 into 10 mM sodium acetate (pH5) containing 5 mM reduced and 0.5 MM oxidized glutathione. After rotating at 37° C. for 2.5 h, the solution was transferred to Spectrum 6 (Fisher) 8000 MW cutoff tubing and dialyzed against 20 volumes of 10 mM sodium acetate (pH 5) for two days. Fresh buffer was provided approximately every 12 hours. The resulting refolded scTCR was concentrated to 1 mg/ml in Centricon 10 micro-concentrators (Amicon) after adding 0.1% CHAPS (Pierce). An example of the product observed under these conditions is seen in lane 4 of FIG. 5.

H. Binding Studies with the FL-scTCR

Several dyes with structures similar to FL are available in forms which allow them to be conjugated to amine-containing substrates. Three of these dyes were chosen and conjugated to Sepharose beads via a 1,6-diaminohexane spacer. The dyes were coupled to the beads as follows. 69 mg of 1,6-dihexylamine (Aldrich) was dissolved in 150 ml of 0.1 M $NaHCO_3$ (pH 8.3) and 0.87 ml ethanolamine was added. 4.4 g of cyanogen bromide activated Sepharose 4B (Pharmacia) that had been swollen as directed by the manufacturer was added to the 1,6-dihexylamine/ethanolamine solution and rotated overnight at 4° C. and then at 37° C. for 1 hour. After washing 5 times with 150 ml PBS, the beads were resuspended and stored at 4° C. as a 1:1 slurry by volume in PBS. Control beads coupled with ethanolamine alone (i.e., without using 1,6-dihexylamine) were prepared in the same manner. The dihexylamine-conjugated beads were coupled to FITC (Molecular Probes), RhITC (rhodamine B isothiocyanate; Aldrich), EITC (eosin-5-isothiocyanate; Molecular Probes); or CNF (5-(and 6-) carboxynapthofluorescein, succininidyl ester; Molecular Probes). An amount (in grams) of each dye equal to its molecular weight$\times 10^{-5}$ was dissolved in 75 $\mu$l of N,N-dimethylformamide and added, with vigorous shaking, to 7.5 ml of 100 mM sodium borate (pH 8.75). This solution was immediately used to resuspend 1 ml of dihexylamine-conjugated beads that had been previously washed with the berate buffer. The tubes were wrapped with aluminum foil and rotated at 4° C. overnight and then for 1 hour at 37° C. The dye-conjugated beads were then washed 3 times with 15 ml 200 mM glycine (pH 8), 2 times with 50% methanol and 3 times with PBS before resuspending and storing as a 1:1 slurry by volume in PBS.

These beads were then used to perform binding studies as follows. 100 $\mu$l of dye (or ethanolamine)-conjugated Sepharose was washed with 1 ml buffer in microcentrifuge tubes (Beckman Instruments). After resuspending in 500 $\mu$l of the same buffer containing 5 $\mu$l (5 $\mu$g) of refolded, concentrated scTCR, the tubes were wrapped in aluminum foil and rotated at 4° C. overnight. After being transferred to fresh microcentrifuge tubes, the beads were washed 3 times with buffer and resuspended in 60 $\mu$l of non-reducing SDS-PAGE sample buffer (same as in section E but without BME). After heating (100° C. for 5 min), 40 $\mu$l samples were separated by SDS-PAGE and proteins were visualized using a Biorad Silver Staining Kit in order to analyze for both dye-specific binding and relative binding of different scTCR forms.

Figure 6:
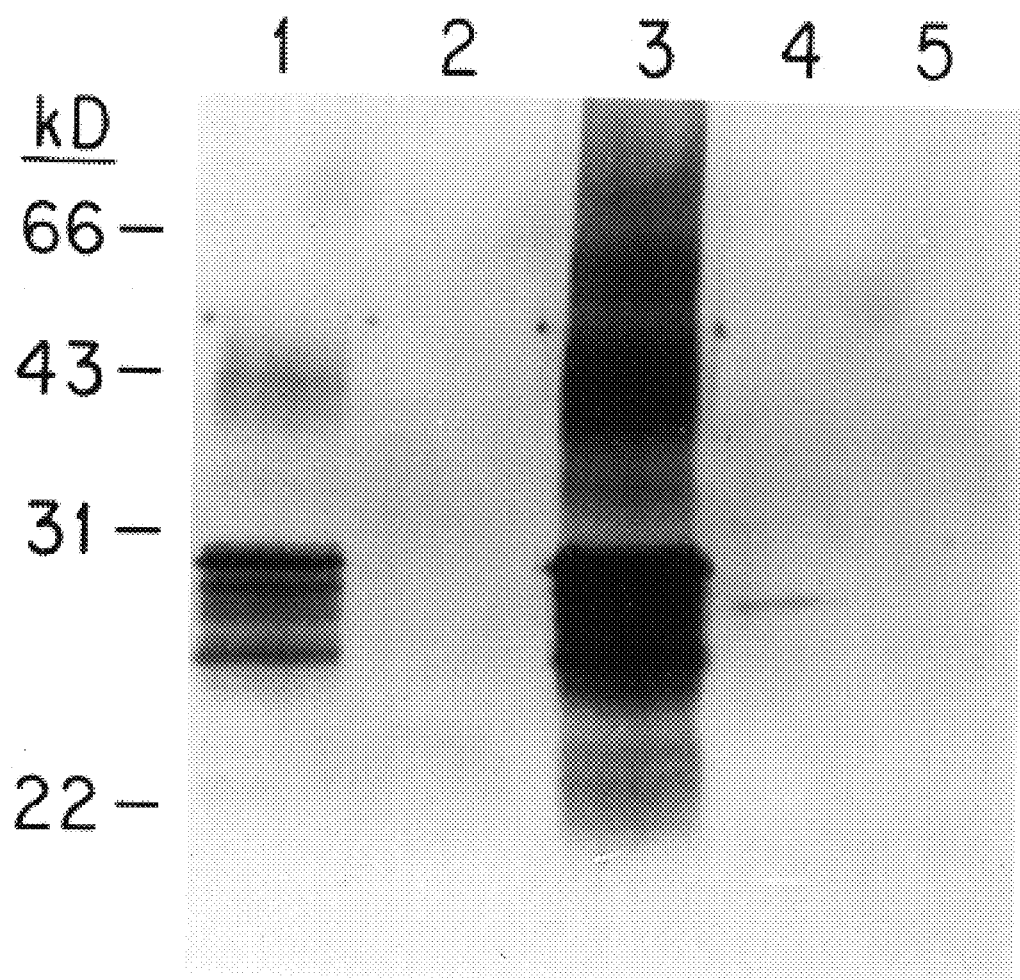
FIG. 6 shows the specific binding of a single chain T cell receptor to fluorescein-coupled Sepharose.

These experiments implicated a band which migrates with an apparent MW of 26 KD as the binding competent form of the scTCR (FIG. 6). This band was over-represented in eluates from FITC-Sepharose beads relative to the distribution of bands seen in the starting material. This over-representation was most apparent when PBS containing NP40 and deoxycholate (DOC) was used as buffer, but was also seen when other detergents were used or when 5 mg/ml bovine serum albumin was utilized instead of detergents. RhITC and ethanolamine coupled beads showed no binding under these conditions, but two control dyes with the same net charge as FITC (EITC and CNF) displayed considerable binding. EITC and CNF, however, apparently interact non-specifically with the protein as, unlike the result with FITC, all forms of the refolded scTCR were bound with similar affinity. The binding of the ~26 KD band to FITC Sepharose could be inhibited by 3 mM 5-(5-amino-pentylthioureidyl)-fluorescein.

EXAMPLE II

Production of Soluble, Single Chain T Cell Receptors Containing Altered Hydrophobic Amino Acid Residues A. Construction of Expression Vector pSS1/FL-scTCR2

In order to increase the solubility of the soluble, anti-fluorescein single chain T cell receptor described in Example I, a number of hydrophobic variable region framework amino acid residues predicted to be surface exposed were replaced with more hydrophilic amino acid residues. The scTCR construct (Isolate #2) described in Example I(C), the nucleotide sequence and deduced amino acid sequence of which is shown in FIG. 2B, was subcloned into the pSS1 secretion vector at Bal I and Pst I sites. pSS1 was created by excising the polylinker (Sac I to Kpn I) of pBluescript II SK⁻ (Stratagene, La Jolla, Calif.) and replacing this region with the pectate lyase B (pelB) leader sequence of *Erwinia carotovora* (with its ribosome binding site) and a new polylinker. The pelB leader was obtained via PCR using pSW1-VHpolyTag1 (See, Ward et al., Nature 341, 544–546 (1989)] as the template. The new polylinker was constructed from two overlapping synthetic oligonucleotides containing restriction sites useful for the subsequent insertion and manipulation of scTCRs. The nucleotide and amino sequences of the polylinker and pel B leader (coding strand only) is as follows:

```
GAGCTCGAAT TCAAATTCTA TTTCAAGGAG ACAGTCATA

ATG AAA TAC CTA TTG CCT ACG GCA GCC GCT
Met Lys Tyr Leu Leu Pro Thr Ala Ala Ala

GGA TTG TTA TTA CTC GCG GCC CAG CCG GCC
Gly Leu Leu Leu Leu Ala Ala Gln Pro Ala

ATG GCC
Met Ala
```

The resultant expression vector (designated pSS1/FL-scTCR1) encodes the pelB leader followed immediately in-frame by Vβ, the "linker" and then Vα segments. The expression of this construct is under the control of the lacZ promoter and is therefore IPTG-inducible. pSS1 based plasmids were maintained in XL1-blue/IQ, a derivative of strain XLI Blue (Stratagene), which contains the plasmid RG1 (obtained from Robert Garcie, Dana Farber Cancer Institute, Boston, Mass.). The latter constitutively expresses lacIQ, a repressor of the lac promoter.

A number of amino acids residues in the expression vector pSS1/FL-scTCR1 were then mutated via site-directed mutagenesis using the Amersham Kit as directed by the manufacturer to generate pSS1/FL-scTCR2. More specifically, the Phe residue at position 10 was changed to a Ser (codon changed from TTC→TCA), the Met residue at position 41 was changed to a Lys (ATG→AAG), the Leu residue at position 111 was changed to a Thr (CTA→ACA), the Ile residue at position 152 was changed to a Arg (ATT→CGT), and the Ile residue at position 146 was changed to a Ser (ATA→TCA) (See, FIG. 2B).

B. Expression of pSS1/FL-scTCR2 in *E. coli*

To induce the expression of the modified scTCR (FL-scTCR2), a 165 ml overnight culture of XLI-Blue containing the pSS1/FL-scTCR2 vector was grown at 37° C. in Luria broth containing 30 μg/ml kanamycin, 50 μg/ml ampicillin and 12.5 μg/ml tetracycline was diluted to 1000 ml with the same media containing 5 mM IPTG. The culture was grown at 37° C., shaking at 250 rpm, for 8 hours. The cell pellet was resuspended in 50 mM Tris-HCl, pH 8.5, 5 mM EDTA, 0.3 mg/ml lysozyme, 1 mM PMSF (phenylmethylsulfonyl fluoride) and incu-bated on ice for 2 hours. NP40 was then added to 0.75% and NaCl to 0.35 M. The suspension was sonicated (Branson 250 sonifier) and centrifuged at 15,000 rpm for 20 minutes. The pellet was resuspended in high salt wash buffer (1.0 M NaCl, 10 mM Tris pH 8.5, 0.5% NP40, 1 mM PMSF, 1 mM EDTA) and repelletted. The process was repeated followed by two washes with low salt wash buffer (10 mM Tris, [pH 8.5], 0.5% NP 40, 1 mM PMSF, 1 mM EDTA). Finally, the pellet was resuspended in 5 ml of solubilization buffer (20 mM Tris (pH 8.0), 50 mM dithiothreitol (DTT), 1 mM PMSF, 8 M urea) and centrifuged for 15 minutes at 15,000 rpm, and the supernate was collected. The urea solubilized FL-scTCR2 was subjected to further purification by reverse phase HPLC on a Vydac C4 column. Chromatography was developed using a gradient of acetonitrile in 0.1% trifluoroacetic acid/water at a flow rate of 1 ml/min. The FL-scTCR2 obtained in this manner was judged to be >95% pure by N-terminal sequence analysis. Fractions containing the FL-scTCR2 were combined, solvent evaporated (Speed Vac) and the pellet was resuspended at a concentration of ~3 mg/ml in 8M urea, 10 mM Tris (pH 8.0) and 20 mM DTT.

It was found that the expression in *E. coli* and the fractionation characteristics of FL-scTCR2 were virtually identical to unmodified scTCR.

C. Solubility Studies of FL-scTCR2

Aliquots containing purified FL-scTCR2 in 8M urea (3 mg/ml) were diluted to 30 μg/ml in 20 mM sodium acetate (pH 5.0), 20 mM sodium phosphate (pH 7.0), PBS (10 mM sodium phosphate [pH 7.4], 150 mM NaCl) or 20 mM Tris-HCl (pH 8.0). Samples were incubated at room temperature for 2 hours, microfuged for 10 minutes and the supernatants analyzed by reducing SDS-PAGE.

It was found that the modified scTCR was substantially more soluble than the unmodified protein. For example, unlike the unmodified protein, FL-scTCR2 was soluble in PBS and in Tris-HCl at neutral pH.

D. Dye-Binding Studies with FL-scTCR2

The antigen specific binding properties of FL-scTCR2 were then tested in neutral pH in physiologic buffer. FITC, RITC, CNF and EITC, were conjugated to Sepharose beads as described herein above.

Dye-conjugated Sepharose beads (100 μl) were washed with PBS in microcentrifuge tubes. 1 ml of PBS containing 10% fetal calf serum was added, the tubes were wrapped in aluminum foil and rotated at 4° C. overnight. After resuspending in 200 μl of the same buffer containing ~15 μg of refolded, concentrated FL-scTCR2, the samples were wrapped in aluminum foil and rotated for 4 hours at room temperature. The beads were then washed with 1 ml of PBS and with 200 μl of PBS. The FL-scTCR2 was eluted by resuspending the beads in 50 μl of PBS containing various concentration (1, 10 or 100 μM) 5-[5-aminopentylthioureidyl]-fluorescein (AP-F1; Molecular Probes). In parallel experiments, 100 μM of AP-F1 was added to RITC- CNF- of EITC-conjugated Sepharose beads. 10 μl of 5×non-reducing SDS-PAGE sample buffer was added to the eluates which were subjected to SDS-PAGE and then transferred to poly-vinylidene difluoride (PVDF, Millipore) membranes. The PVDF blots were incubated with affinity-purified anti-FL-scTCR antibody followed by alka-line phosphatase conjugated goat anti-mouse IgG (Biorad, Richmond, Calif.) and developed by adding a solution of 5-bromo-4-chloro-3-indolyl phosphate disodium salt and p-nitroblue tetrazolium chloride (Biorad, Richmond, Calif.). Polyclonal antisera against the scTCR had been raised by immunizing rabbits with purified FL-scTCR1, and specific antibodies were purified by affinity chromatography using Affigel 10 beads (Pierce) coupled with purified FL-scTCR1.

It was found that a single band at ~29 KD was eluted by 100 $\mu$M AP-F1 from FITC Sepharose. In contrast, no band was eluted from RITC-, CNF- or EITC-conjugated Sepharose beads. The 29 KD species could not be eluted from FITC-Sepharose by RITC, further supporting the specificity of the FL-scTCR2 for fluorescein. Of note is the fact that neither the oligomers in the refolded FL-scTCR2 preparation nor the most rapidly migrating species at 17 KD were specifically elutable from FITC conjugated Sepharose. These findings imply that only the 29 KD FL-scTCR2 protein has an antigen binding property. We take this as evidence for the nativity of the V$\beta$ and V$\alpha$ domains in this species of the refolded scTCR mixture.

DETAILED DESCRIPTION OF THE DRAWINGS

FIG. 1: Polypeptide backbone tracing of two computer generated models of the single-chain T cell receptor with anti-fluorescein specificity. The structures are representative examples selected from the trajectory of molecular dynamics simulation used to generate a set of approximate structural models. Models are presented in a side view, with the hypervariable loops (heavy lines) pointing to the right. The variable-$\beta$ domain is on the top, variable- domain on the bottom (backbones traced by dotted lines). Part of the linker structure is clearly visible as a protrusion, from the variable-$\beta$ domain, in the upper left corner of the picture.

FIG. 2A: Schematic indicates order of the TCR domains and peptide linker segments. For the periplasmic secretion system, the junctional sequences between the phoA leader and the single chain TCR are given for TCR1 and TCR2. The empirically derived amino acid sequences of individual proteins are indicated. FIG. 2B: Nucleotide and amino acid sequence of the FL-specific scTCR.

FIG. 3: Maps of plasmids pTCR $\beta$-ILE$_{182}$ and pTCR $\beta$-MET$_{182}$. These plasmids are derived from pBR322. The single chain T cell receptor chimeric fragment was cloned into the Eco RI and Pvu II sites of pBR322. Both plasmids are approximately 3.0 kB and differ from one another only in one nucleotide position. The positions of several restriction enzyme cleavage sites are shown. The DNA sequences derived from the $\beta$ chain are shown as dark bars and the sequences derived from the chain are shown as hatched bars. Amp$^V$=bacterial gene conferring ampicillin resistance. Ori=pBR322 origin of replication.

FIG. 4: Scale drawings depicting single chain T cell receptor encoding DNA fragments. A. DNA fragment cloned in isolate #2 encodes a chimeric protein where residue 182 is an isoleucine. B. DNA fragment cloned in isolate #5 encodes a methionine at position 182. The methionine codon is part of a Bal I restriction site (ATGGCCA, where the methionine codon is shown in bold type and the Bal I site is underlined). Digestion with this enzyme can distinguish between the two isolates. The $\beta$ chain derived segment is shown boxed and the chain segment is indicated with hatch-marks. The black segment in the middle represents the "linker" sequence.

FIG. 5: Purification of scTCR. Total cell lysate, 1; urea extract of insoluble precipitable material in cell lysate, 2;

RPHPLC purified and refolded scTCR (0.5 $\mu$g), 3; RPHPLC purified and refolded scTCR (3 $\mu$g), 4. Lanes 1, 2 and 3 were run under reducing conditions, lane 4 under non-reducing conditions.

FIG. 6: Specific binding of a scTCR species to FITC-coupled Sepharose. scTCR was eluted from Sepharose beads coupled with: CNF, 1; RhITC, 2; EITC, 3; FITC, 4; ethanolamine, 5.

What is claimed is:

1. A soluble, single chain T cell receptor encoded by the nucleic acid sequence as shown in FIG. 2B.

2. A soluble, single chain polypeptide comprising a Ti $\beta$ subunit fragment joined to a Ti $\alpha$ subunit fragment by an amino acid linker wherein said Ti $\beta$ subunit fragment comprises amino acids 1 through 111 as shown in FIG. 2B, said Ti $\alpha$ subunit fragment comprises amino acids 135 through 246 as shown in FIG. 2B, and said amino acid linker comprises amino acid residue 112 through 134 as shown n FIG. 2B.

3. The soluble, single chain polypeptide of claim 2 which is biologically active.

4. The soluble, single chain polypeptide of claim 2 which is soluble in aqueous solution.

5. The soluble, single chain polypeptide of claim 2 which has been derivatized.

6. The soluble, single chain polypeptide according to claim 5 which has been derivatized by labeling with a radioisotope.

7. The soluble, single chain polypeptide according to claim 5 which has been derivatized by conjugation to a toxin.

8. The soluble, single chain polypeptide of claim 2 which binds at least one antigen which is bound by a T cell receptor present on the surface of a T lymphocyte of mammalian origin.

9. A DNA molecule having a nucleic acid sequence of FIG. 2B.

10. An expression vector comprising a DNA molecule having a nucleic acid sequence of FIG. 2B.

11. The expression vector according to claim 10 comprising one or more control DNA sequences capable of directing the replication and/or the expression of and operatively linked to a DNA sequence coding for a soluble, single chain T cell receptor.

12. A prokaryotic or eukaryotic host cell containing the expression vector according to claim 10.

13. A prokaryotic or eukaryotic host cell containing the expression vector according to claim 10 or 11.

14. The host cell according to claim 12 wherein the host cell is a bacterial cell.

15. The host cell according to claim 14 wherein the bacterial cell is an *Escherichia coli* cell.

16. A method for producing a soluble, single chain polypeptide comprising culturing a host cell according to claim 12 under conditions permitting expression of the soluble, single chain T cell receptor.

* * * * *